US012672965B2

(12) United States Patent
Frigg et al.

(10) Patent No.: US 12,672,965 B2
(45) Date of Patent: Jul. 7, 2026

(54) EXPANDABLE INTERVERTEBRAL CAGE

(71) Applicant: 25SEGMENTS, Zürich (CH)

(72) Inventors: Robert Frigg, Bettlach (CH); Daniel Fluri, Grenchen (CH); Mazda Farshad, Zumikon (CH); Patrick Burki, Solothurn (CH)

(73) Assignee: 25SEGMENTS AG, Zürich (CH)

( * ) Notice: Subject to any disclaimer, the term of this patent is extended or adjusted under 35 U.S.C. 154(b) by 146 days.

(21) Appl. No.: 18/561,548

(22) PCT Filed: May 11, 2022

(86) PCT No.: PCT/EP2022/062781
§ 371 (c)(1),
(2) Date: Nov. 16, 2023

(87) PCT Pub. No.: WO2022/243133
PCT Pub. Date: Nov. 24, 2022

(65) Prior Publication Data
US 2024/0245527 A1 Jul. 25, 2024

(30) Foreign Application Priority Data

May 17, 2021 (CH) ..................................... 00549/21
Feb. 14, 2022 (CH) ................................ 000135/2022

(51) Int. Cl.
*A61F 2/44* (2006.01)
*A61F 2/30* (2006.01)

(52) U.S. Cl.
CPC .... *A61F 2/447* (2013.01); *A61F 2002/30398* (2013.01); *A61F 2002/30411* (2013.01);
(Continued)

(58) Field of Classification Search
CPC .......... A61F 2/447; A61F 2/44; A61F 2/4461; A61F 2002/30398; A61F 2002/30411;
(Continued)

(56) References Cited

U.S. PATENT DOCUMENTS 11,517,363 B2 * 12/2022 Nayet .................... A61F 2/4455
11,517,443 B2 * 12/2022 Dewey .................. A61F 2/4425
(Continued)

FOREIGN PATENT DOCUMENTS

JP 2014-180551 A 9/2014
WO WO-2015063721 A1 * 5/2015 ............ A61F 2/4611
(Continued)

OTHER PUBLICATIONS

EPO (Rijswijk, NL), English version of the International Search Report, Form PCT/ISA/210, for International Application PCT/EP2022/062781, Sep. 14, 2022 (3 pp.).
(Continued)

*Primary Examiner* — Jessica Weiss
(74) *Attorney, Agent, or Firm* — Pauley Erickson & Swanson

(57) ABSTRACT

An expandable intervertebral cage includes a base with a circumferential side wall extending in a first direction and a first bone interaction surface and a stage including a second bone interaction surface arranged essentially opposite to the first bone interaction surface with respect to the expandable intervertebral cage. An expansion mechanism serves for adjusting the position of the second bone interaction surface of the stage with respect to the first bone interaction surface of the base at least in the first direction (z). The expansion mechanism is thereby arranged at least partially within the circumferential side wall of the base.

12 Claims, 5 Drawing Sheets

(52) U.S. Cl.
CPC ............... *A61F 2002/30507* (2013.01); *A61F 2002/30556* (2013.01); *A61F 2002/30784* (2013.01)

(58) Field of Classification Search
CPC .. A61F 2002/30507; A61F 2002/30556; A61F 2002/30784
USPC .......................................... 623/17.11–17.16
See application file for complete search history.

(56) References Cited

U.S. PATENT DOCUMENTS

| | | | | |
|---|---|---|---|---|
| 11,554,021 B2 * | 1/2023 | Kuyler | .................... | A61F 2/447 |
| 11,596,524 B2 * | 3/2023 | Kuyler | ................... | A61F 2/4455 |
| 11,612,499 B2 * | 3/2023 | Barfield | ............... | A61F 2/4455 |
| | | | | 623/17.16 |
| 11,638,653 B2 * | 5/2023 | Nayet | .................. | A61B 17/862 |
| | | | | 606/80 |
| 11,759,334 B2 * | 9/2023 | Klausman | ............. | A61F 2/4611 |
| | | | | 623/17.16 |
| 11,793,651 B2 * | 10/2023 | Berry | ...................... | A61F 2/442 |
| 11,806,250 B2 * | 11/2023 | Miller | .................. | A61F 2/4455 |
| 11,833,059 B2 * | 12/2023 | Josse | ................... | A61F 2/30749 |
| 11,963,881 B2 * | 4/2024 | Josse | .................... | A61F 2/4611 |
| 12,121,453 B2 * | 10/2024 | Dewey | ................. | A61F 2/4425 |
| 2006/0122703 A1 * | 6/2006 | Aebi | .................... | A61F 2/4425 |
| | | | | 623/17.15 |
| 2007/0135919 A1 * | 6/2007 | Aebi | .................... | A61F 2/4425 |
| | | | | 623/17.11 |
| 2010/0004749 A1 * | 1/2010 | Beger | .................. | A61F 2/4425 |
| | | | | 623/17.16 |
| 2013/0158669 A1 * | 6/2013 | Sungarian | ............... | A61F 2/442 |
| | | | | 623/17.16 |
| 2017/0156885 A1 | 6/2017 | Zur et al. | | |
| 2018/0193164 A1 | 7/2018 | Shoshtaev | | |
| 2019/0274837 A1 * | 9/2019 | Eisen | ................... | A61F 2/4611 |
| 2019/0307577 A1 | 10/2019 | Predick et al. | | |
| 2020/0281741 A1 * | 9/2020 | Grotz | .................... | A61F 2/447 |
| 2020/0383798 A1 | 12/2020 | Butler et al. | | |

FOREIGN PATENT DOCUMENTS

| | | |
|---|---|---|
| WO | WO 2015/198335 A1 | 12/2015 |
| WO | WO 2016/019241 A1 | 2/2016 |
| WO | WO 2019/170739 A1 | 9/2019 |

OTHER PUBLICATIONS

EPO (Munich, DE), English version—Written Opinion of the Int'l Searching Auth., Form PCT/ISA/237, for International Application PCT/EP2022/062781, Sep. 14, 2022 (9 pp.).

Japanese Patent Office (JPO), Japanese language Office Action, Japanese Patent Application No. 2023-571558, issued Feb. 13, 2026 (5 pages).

* cited by examiner

EXPANDABLE INTERVERTEBRAL CAGE

CROSS REFERENCE TO RELATED APPLICATION

This application is a National Phase filing in the United States, under 35 USC § 371, of PCT International Patent Application PCT/EP2022/062781, filed on 11 May 2022 which claims the priority of Swiss Patent Application No. CH 00549/21, filed 17 May 2021 and Swiss Patent Application No. CH 000135/2022, filed 14 Feb. 2022.

The above-referenced applications are hereby incorporated by reference herein in their entirety and are made a part hereof, including but not limited to those portions which specifically appear hereinafter.

BACKGROUND OF THE INVENTION

Field of the Invention

The present disclosure relates to an expandable intervertebral cage. The expandable intervertebral cage, hereinafter also referred to as cage, can be brought as an implant into an intervertebral space in a retracted state, and once in place, can be expanded continuously to a desired expanded state.

Discussion of Related Art

Vertebrae are the individual irregular bones that make up the spinal column, which under normal circumstances is a flexuous and flexible column. There are normally thirty-three vertebrae in humans, including the five that are fused to form the sacrum (the others being separated by intervertebral discs) and the four coccygeal bones which form the tailbone. The upper three regions comprise the remaining 24 vertebrae, which are grouped under the names cervical (7 vertebrae), thoracic (12 vertebrae) and lumbar (5 vertebrae), according to the regions they occupy.

From the prior art various devices are known, which can be inserted between two adjacent vertebrae to control their distance and the spacing between them. These devices may be used on a temporary basis, such as during surgery when it is e.g., necessary to access the specific surfaces of the vertebral members. The devices may also remain as implants permanently within the patient to stabilize the vertebral members. These kinds of permanent devices may be for instance fusion cages that provide a filling room for inserting a bone graft between adjacent portions of a bone. Over time, the bone and bone graft grow together through or around the fusion cage to fuse the graft and the bone solidly together. One current use of fusion cages is to treat a variety of spinal disorders, including degenerative disc diseases, such as Grade I or II spondylolistheses of the lumbar spine. Spinal fusion cages (included in the general term "fusion cages") are inserted into the intervertebral disc space between two vertebrae for fusing them together. They expand (or distract) a collapsed disc space between two vertebrae to stabilise the vertebrae by preventing them from moving relative to each other. Application of an intervertebral cage for fusion of a spine segment in addition to pedicle screws typically increases fusion rates between 10% and 15%. Larger cages, as implanted by lateral or anterior approaches can even be inserted in the intervertebral space stand-alone without addition of pedicle or other screws, and they provide a sufficient mechanical base for a solid fusion.

An example of an expandable intervertebral cage is disclosed in WO 16019241 A. The intervertebral cage comprises an upper bar and an opposing lower bar and a separator movable between the upper bar and the lower bar to cause movement of the upper bar towards and away from the lower bar. The intervertebral cage further comprises a pin having a first end extending into an opening provided in the upper bar and a second end extending into an opening provided in the second bar.

A further example of a cage with an integrated expansion and angular adjustment mechanisms is disclosed in the WO 19170739 A1. The herein described mechanisms allows the cage to change its height and angle as needed. The expansion and angular adjustment mechanism is disposed between an upper and lower housing portion with sidewalls configured to slide along each other. A pair of drivable wedges are located on of the housing to engage with respective engagement surfaces of the sidewalls. Hence, if the wedges are moved toward each other, engagement surfaces of the wedges bear against the respective engagement surfaces of the sidewalls, thereby moving the upper and lower housing away from each other.

SUMMARY OF THE INVENTION

The surgical challenge of placement of an intervertebral cage is usually the limited available approach space due to bony structures, such as the endplates or the facet joints, and nervous structures, such as the dural sac and nerve roots, for dorsal approaches, and additionally by vascular structures for anterior or lateral approaches. The most commonly used approaches to place a cage are dorsal in nature, and often referred to as posterior lumbar interbody fusion (PLIF) or transforaminal lumbar interbody fusion (TLIF). For both approaches, the nerve root and the dural sac are retracted medially to be able to open the disc space to allow removal of the disc before inserting the intervertebral cage. An intervertebral cage has thus very limited dimensions in order to fit into said disc space. Furthermore, once fitted the intervertebral cage needs to be accessed (usually one sided) in order to be expanded through an expansion mechanism.

As mentioned above, expandable intervertebral cages are known from the prior art, however, these devices typically have a rather complex structure and there is often a risk of accidentally collapsing them, when in the intervertebral space, as they are not self-stable. A further problem of the currently available expandable intervertebral cages is that they do often not allow to take the patient's lordosis angle into account. This is due to the fact, that known intervertebral cages can adapt only in height. Often the individual vertebrae alignment is usually too large and therefore requires an even more complex expansion mechanism.

The present disclosure overcomes these problems by providing a simple but robust and versatile intervertebral cage with a shallow design that allows the cage to be inserted into the intervertebral disc space in a minimally invasive manner through a comparatively small opening with respect to the prior art. Once inserted, the intervertebral cage can be expanded to adjust the spacing between adjacent vertebrae. Furthermore, the present disclosure relates to an intervertebral cage that is adaptable to the patient's lordosis angle. If appropriate, it is also possible to arrange more than one intervertebral cages according to the present disclosure next to each other and to adjust each of them to a required position.

An expandable intervertebral cage according to the disclosure is designed to fold into itself in a retracted state thereby being very shallow and having only a limited height compared to the products known from the prior art. Due to the special design, which will be explained in more detail hereinafter, it is possible to design the intervertebral cage such that it can double the height when expanded. The initial height, when retracted, is e.g., 7 mm and can be expanded to approximately 14 mm. This ability to expand the cage from the retracted state allows the cage to be inserted through a much smaller opening than what is possible with rigid fusion cages, while providing the same final spacing between the vertebrae as provided by rigid fusion cages.

Furthermore, when expanded, the intervertebral cage opens up and thereby allows insertion of sufficient bone graft within the cage to allow intersomatic fusion. In this manner, bone graft can be inserted in a filling room of the (expanded) cage to aid in the fusion of the adjacent vertebrae. In a preferred variation the cage allows continuous change of height while keeping sufficient mechanical stability. Depending on the design, the intervertebral cage comprises a self-locking mechanism e.g., formed by two interconnected drive shafts and associated nut elements. In this manner, the height of the intervertebral cage is maintained in any of its expanded state by self-locking. In this manner, any inadvertent collapse of the cage is prevented while in the intervertebral disc space. Furthermore, the cage can be dimensioned so that it can be used to correct lordosis, as explained in more detail hereinafter.

According to the disclosure, such an expandable intervertebral cage usually comprises a base and a with respect to the base in a first direction linear displaceable stage. The base and the stage are interconnected to each other by an expansion mechanism which is primarily arranged (integrated) within the base and/or the stage when the intervertebral cage is in a retracted state. The base and the thereto displaceable stage each comprise a bone interaction surface (first and second bone interaction surface). The second bone interaction surface is arranged essentially opposite to the first bone interaction surface with respect to the expandable intervertebral cage.

The base preferably comprises a circumferential side wall extending in the first direction away from the bone interaction surface of the base. Hereby, the bone interaction surface may be arranged on a bottom wall of the base. Thus, the circumferential side wall may extend in the first direction away from the bottom wall. The circumferential side wall and/or the bottom wall can further be thin-walled. Hence, the base may be trough-shaped. Such a structure serves for a high stiffness of the cage while offering at the same time a large interior space for the expansion mechanism and the filling room for the bone graft. If appropriate, the first bone interaction surface can be arranged essentially perpendicular to the circumferential side wall. The circumferential side wall is preferably arranged peripherally. As described hereinafter in more detail in connection with the accompanying drawings, the circumferential side wall supports and protects the expansion mechanism arranged on its inside. A very shallow setup with a low profile in the retracted state can be achieved when the circumferential side wall encompasses an inner space in which the expansion mechanism is arranged in the retracted state. The circumferential side wall can e.g., have a circular and/or oval and/or rectangular layout or a combination thereof. Depending on the application, the first bone interaction surface and/or the second bone interaction surface may circumvent at least partly an opening for a filling room for accommodating bone graft. Advantageously, the first bone interaction surface and/or the second bone interaction surface is ring-shaped circumventing said opening.

By the expansion mechanism the stage is continuously linear displaceable with respect to the base in the first direction between the retracted state and at least one expanded state. The respective expanded states are spaced a distance apart from the retracted state and determine a total working height (distance between the first and the second bone interaction surface) of the intervertebral cage. Depending on the design, the expansion mechanism may further be configured to position the second bone interaction surface with respect to the first bone interaction surface in at least one further direction, in particular around the tilting axis. In that case the second bone interaction surface of the stage is tiltable, in particular continuously tiltable, with respect to the first bone interaction surface of the base, such that a tilting angle is formed between the first and second bone interaction surface. Depending on the design, the tilting angle can be adjusted independently from the linear displacement of the stage with respect to the base. In other variations, the tilting angle may be coupled to the linear displacement by a certain gear ratio. Depending on the individual design of the cage, the tilting axis may be arranged within or outside of the contour of the expandable intervertebral cage.

In a preferred variation, the expansion mechanism comprises a first lever and a thereto opposite second lever. Each lever is interconnected by a base swivel joint to the base and by a stage swivel joint to the stage. Usually, the base swivel joint and the stage swivel joint are arranged at opposite ends of the respective lever. The inner space encompassed by the circumferential side wall is sufficient large to receive both levers in the retracted state. In a preferred variation, the first and the second lever are in the retracted state arranged behind each other extending essentially in the same direction. If appropriate the first and the second lever may be slightly bend with respect to each other in the retracted state. Furthermore, the second lever may have a different length than the first lever (or vice versa).

A very robust and versatile arrangement can be achieved when the base swivel joint of each lever is arranged displaceable with respect to the base swivel joint of the opposite lever. Alternatively, the stage swivel joint of the first lever and the stage swivel joint of the second lever may be displaceable with respect to each other. In a preferred variation, each base swivel joint is arranged linearly displaceable. Therefore, each base swivel joint can be arranged in respective guiding slot arranged in the circumferential side wall extending in a second direction essentially perpendicular to the first direction. Thereby, the base swivel joint of the first lever is linearly displaceable by a first displacement distance and the base swivel joints of the second lever is linearly displaceable by a second displacement distance. Depending on the application the first and the second displacement distances can have different lengths. In a preferred variation, the base swivel joints comprise each two pivot bolts arranged coaxially and opposite with respect to each other extending in a third direction perpendicular to the first and the second direction. Preferably, also the before mentioned tilting axis extends in said third direction. The pivot bolts are arranged linearly displaceable in the second direction with respect to each other. Good results can be achieved, when the circumferential side wall comprises two pairs of opposite guiding slots, one pair for each lever. One pair of guiding slots is thus arranged opposite and coaxially of each other in the third direction with respect to the circumferential side wall. In order to provide different displacement distances of the base swivel joints, also the respective guiding slots of the first and second levers may have different lengths. Hence, one lever can extend higher than the other lever and the tiling angle is established.

To displace the base swivel joints of each lever the expansion mechanism can comprise a first thread having a positive thread direction and a thereto coaxially arranged second thread having a negative thread direction (or vice-versa). The first and the second thread rotate around a center axis extending in the second direction. The first thread may thereby be interconnected to the base swivel joint of the first lever and the second thread may be interconnected to the base swivel joint of the second lever to displace the base swivel joints with respect to each other. Hence, by operating a respective thread, the interconnected base swivel joint is displaced within the guiding slot, which in turn pushes the interconnected lever and expands the cage. The first and second thread may further have the same or a different thread pitch. However, for a fine and controlled tuning of the cage expansion threads having the same thread pitch are more desirable. Depending on the application, the first and the second thread may be interconnected to each other in a torque proof manner. This is in particular advantageous for expandable intervertebral cages that are only adjustable in the first direction, respectively that are adjustable in height. To realize a further tilting movement, the first and the second thread are preferably arranged rotatable relative to each other. This allows that the first and the second thread to operate simultaneously or independently from each other. Hence, by e.g., rotating only the second thread, only the second lever is extended and the second bone interaction surface, respectively the stage, is tilted with respect to the first bone interaction surface, respectively the base (or vice versa).

In a preferred variation, a first nut is arranged on the first thread to interconnect the base swivel joint of the first lever to the first thread. A second nut is arranged correspondingly on the second thread to interconnect the base swivel joint of the second lever to the second thread. The interconnection through nuts is advantageous, since the nut can (self-)lock the cage in each expanded stage preventing collapsing of the cage. By operating a respective thread, the nut on the thread is displaced, which in turn pushes the interconnected lever up thereby displacing the base swivel joint within the guiding slot. In order to rotate the first and the second thread relatively to each other, the second thread can extend into a shaft on which a bushing is arranged at least partly on said shaft. Meanwhile, the bushing can comprise the first thread on an outer surface of said bushing. The shaft and the bushing are preferably arranged coaxially with respect to each other, thereby both preferably extend in the second direction. Hereby, the shaft may extend from a distal end towards a free end, whereon the bushing is arranged. By rotating the bushing (respectively the first thread) and the shaft (respectively the second thread) simultaneously, the second bone interaction surface is continuously displaced from the first bone interaction surface. However, by rotating the bushing (respectively the first thread) and the shaft (respectively the second thread) separately from each other the second bone interaction surface is continuously tilted with respect to the first bone interaction surface.

As stated above, the expansion mechanism is primarily arranged (integrated) within the circumferential side wall of the base. Therefore, a distal end of the bushing can be mounted in a first bearing opening of the circumferential side wall, meanwhile the distal end of the shaft may be pivotably mounted in a second bearing opening of the circumferential wall. Thus, the first and the second opening are arranged opposite of each other with respect to the circumferential side wall.

In order to rotate the respective thread(s) and adjust the position of the first and second bone interaction surfaces with respect to each other, the distal end of the bushing can comprise a first tool interface and the free end of the shaft can comprise a second tool interface. The first and second tool interface serve to operate the expansion mechanism with the tool. Hereby, the first tool interface is preferably arranged adjacent to the second tool interface and may be configured to be operated by the same tool than the first tool interface. The circumferential side wall may comprise an opening in the second direction such that the first and/or second tool interfaces are assessable with the respective tool. The opening for the first and/or second tool interfaces can be the first bearing opening. The second tool interface can be arranged inside a contour of the first tool interface from a view along the second direction. The first and/or the second tool interface may further have a hexalobular shape from a view along the second direction. Thus, the first tool interface may have a hexalobular shaped inner surface, meanwhile the second tool interface may have a hexalobular shaped outer surface. Hereby, the inner surface faces in a radial inwards direction, meanwhile the outer surface faces in a radial outwards direction. Thereby, the inner surface may be arranged within the distal end of the bushing. The outer surface can be arranged circumferentially around the free end of the shaft. Good results are achieved, if the first and/or second tool interface is compatible with a Torx tool, respectively a Torx interface is used.

Alternatively, or in addition, the first and second tool interface may be arranged consecutively in the second direction. E.g., the second tool interface can be arranged further away from a center of the cage in the second direction than the first tool interface. It is also possible, that either the first or the second tool interface or both (the first and the second tool interface) protrude from the circumferential side wall in a with respect to the cage outwards direction. It is thus possible that the second tool interface is arranged at least partly outside of the circumferential side wall, meanwhile the first tool interface is arranged inside of the circumferential side wall.

Depending on the application, the intervertebral cage may further comprise at least one positioning interface for positioning of the tool with respect to the cage. The tool interconnected to the at least one positioning interface may thereby help to position the tool with respect to the first and/or second tool interface. Furthermore, the at least one positioning interface can prevent undesired tipping of the cage with respect to the tool. Preferably, two positioning interfaces are arranged opposite from each other with respect to the first and/or second tool interface. Furthermore, the two positioning interfaces can be arranged adjacent to respective opposite edges of the circumferential wall. For easy operating of the cage, the at least one positioning interface is accessible from the second direction. Hereby, the at least one positioning interface may be a recess in the second direction. In that case, the tool can at least partly engage into said recess during positioning of the cage between the vertebrae. Alternatively, the respective positioning interface(s) may be a protrusion and/or a guide rail arranged on the circumferential side wall and preferably extending in the second direction.

Depending on the application, a further locking element can be arranged on the circumferential side wall. The locking element serves for temporarily interconnecting the tool and the intervertebral cage in the second direction. Thus, the locking element prevents that the cage accidentally slips from the tool during insertion and may further serve for positioning of the cage between the vertebrae. For an easy operation of the cage, the locking element is preferably accessible from the second direction. Thus, the locking element may be arranged next to the tool interface(s) and/or between the two positioning interfaces in a third direction. According to one variation, the locking element may comprise a latch or an undercut (in the second direction) configured such that a respective latch of the tool may be (temporarily) latched behind the undercut. Alternatively, the locking element may comprise a thread. The thread can be arranged in a (threaded) hole extending in the circumferential side wall. In that case, a part of the tool may be screwed into the threaded hole in order to interconnect the tool and the intervertebral cage in the second direction such that the cage cannot accidentally slip from the tool.

Depending on the application, the expandable intervertebral cage can comprise an additional linear guiding structure to prevent unwanted lateral tilting, e.g., in intermediate positions. The linear guiding structure stabilizes the intervertebral cage in an expanded state and prevents unwanted movements in lateral direction. The linear guiding structure can be designed as at least one strut extending from the stage into the circumferential side wall. The (second) bone interaction surface of the stage may be arranged on an upper wall. The at least one strut can thus extend from the upper wall into the circumferential side wall of the base. As explained above, the upper wall and/or the bottom wall can be ring-shaped circumventing the opening for the filling room. Preferably the at least one strut extends along an inner side wall of the circumferential side wall such that the side wall further supports the strut. The strut may comprise a notch extending in a longitudinal direction of the strut and interconnected to the circumferential side wall by a pin configured to slide in the notch and/or rotate with respect to the notch within the notch. E.g., if the cage is in a tilted (respectively the second bone interaction surface has a tilting angle to the first bone interaction surface) the pin remains in the notch rotated with respect to the notch. For an improved stabilization, the linear guiding structure comprises at least two struts arranged opposite with respect to each other on the circumferential side wall. Preferably, the two struts are arranged opposite of each other in the third direction in order to further stabilize the tilting axis extending is said direction. An arrangement of the two struts between the first and second lever in the second direction is further advantageous.

It is to be understood that both the foregoing general description and the following detailed description present embodiments, and are intended to provide an overview or framework for understanding the nature and character of the disclosure. The accompanying drawings are included to provide a further understanding, and are incorporated into and constitute a part of this specification. The drawings illustrate various embodiments, and together with the description serve to explain the principles and operation of the concepts disclosed.

BRIEF DESCRIPTION OF SEVERAL VIEWS OF THE DRAWINGS

The herein described disclosure will be more fully understood from the detailed description given herein below and the accompanying drawings which should not be considered limiting to the disclosure described in the appended claims. The drawings are showing:

DETAILED DESCRIPTION OF THE INVENTION

Reference will now be made in detail to certain embodiments, examples of which are illustrated in the accompanying drawings, in which some, but not all features are shown. Indeed, embodiments disclosed herein may be embodied in many different forms and should not be construed as limited to the embodiments set forth herein; rather, these embodiments are provided so that this disclosure will satisfy applicable legal requirements. Whenever possible, like reference numbers will be used to refer to like components or parts.

Figure 1:
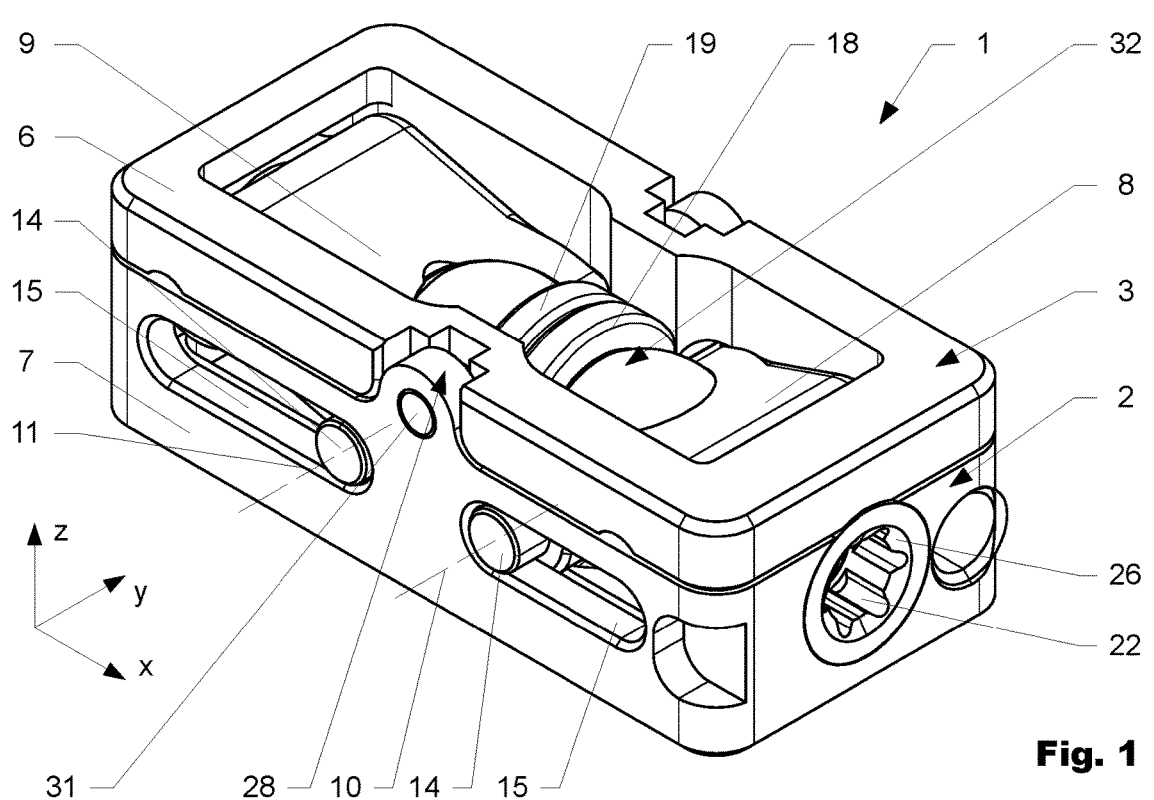
FIG. 1 shows a first variation of an expandable intervertebral cage in a retracted state in a perspective view.
Figure 2:
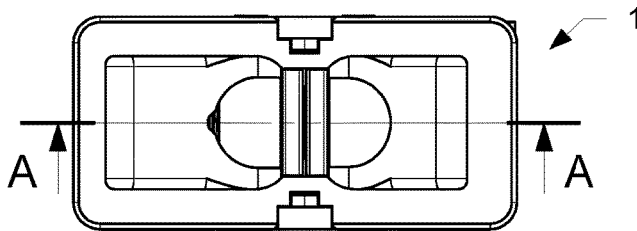
FIG. 2 shows the expandable intervertebral cage according to FIG. 1 in a top view.
Figure 3:
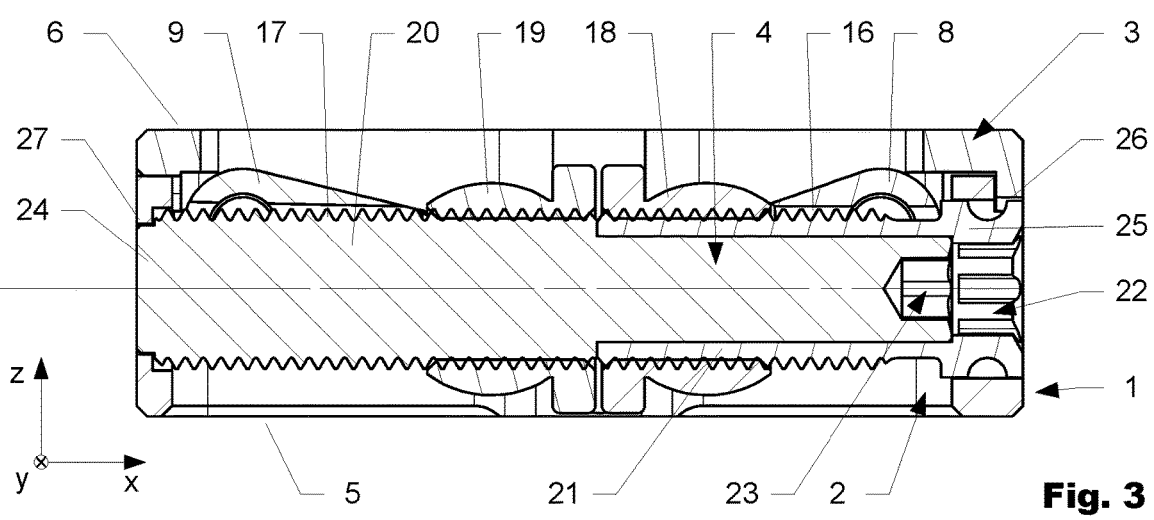
FIG. 3 shows the expandable intervertebral cage in a sectionized view A-A according to FIG. 2.

FIG. 17 show a first variation of an expandable intervertebral cage 1 according to the disclosure. The expandable intervertebral cage 1 comprises a base 2 and a stage 3. The base comprises a peripheral circumferential side wall 7 extending in a first direction (z-direction) and a first bone interaction surface 5, meanwhile the stage 3 comprises a second bone interaction surface 6 arranged essentially opposite to the first bone interaction surface 5 with respect to the expandable intervertebral cage 1. In order to displace and/or tilt the stage 3 with respect to the base 2 an expansion mechanism 4 is used. The expansion mechanism 4 serves for adjusting the position of the second bone interaction surface 6 of the stage 3 with respect to the first bone interaction surface 5 of the base 2. The expansion mechanism 4 is integrated within the base 2 and the stage 3, when the intervertebral cage is in a retracted state. In the retracted state, as illustrated in FIG. 3, the expansion mechanism 4 is arranged at least partially within the circumferential side wall 7 of the base 2. In the shown embodiment the expansion mechanism 4 not only serves to adjust the height of the cage 1, but further is able adjust the position of the second bone interaction surface 6 of the stage 3 with respect to the first bone interaction surface 5 of the base 2 around a tilting axis.

Figure 4:
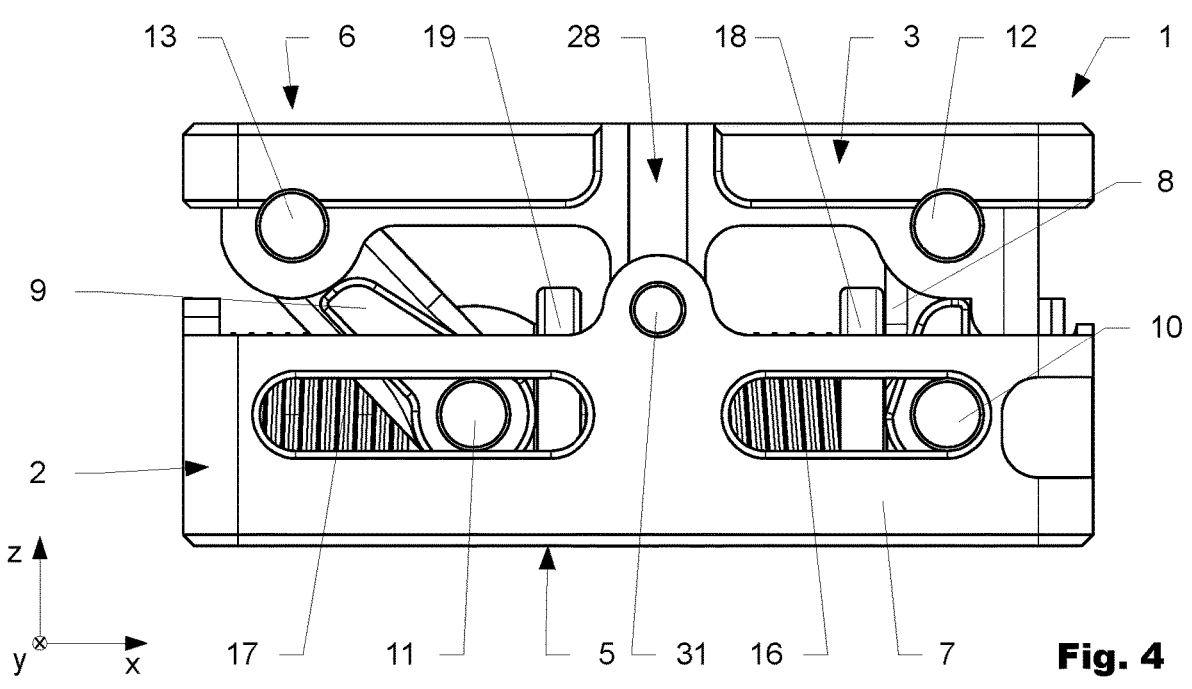
FIG. 4 shows the expandable intervertebral cage in an expanded state in a side view.
Figure 5:
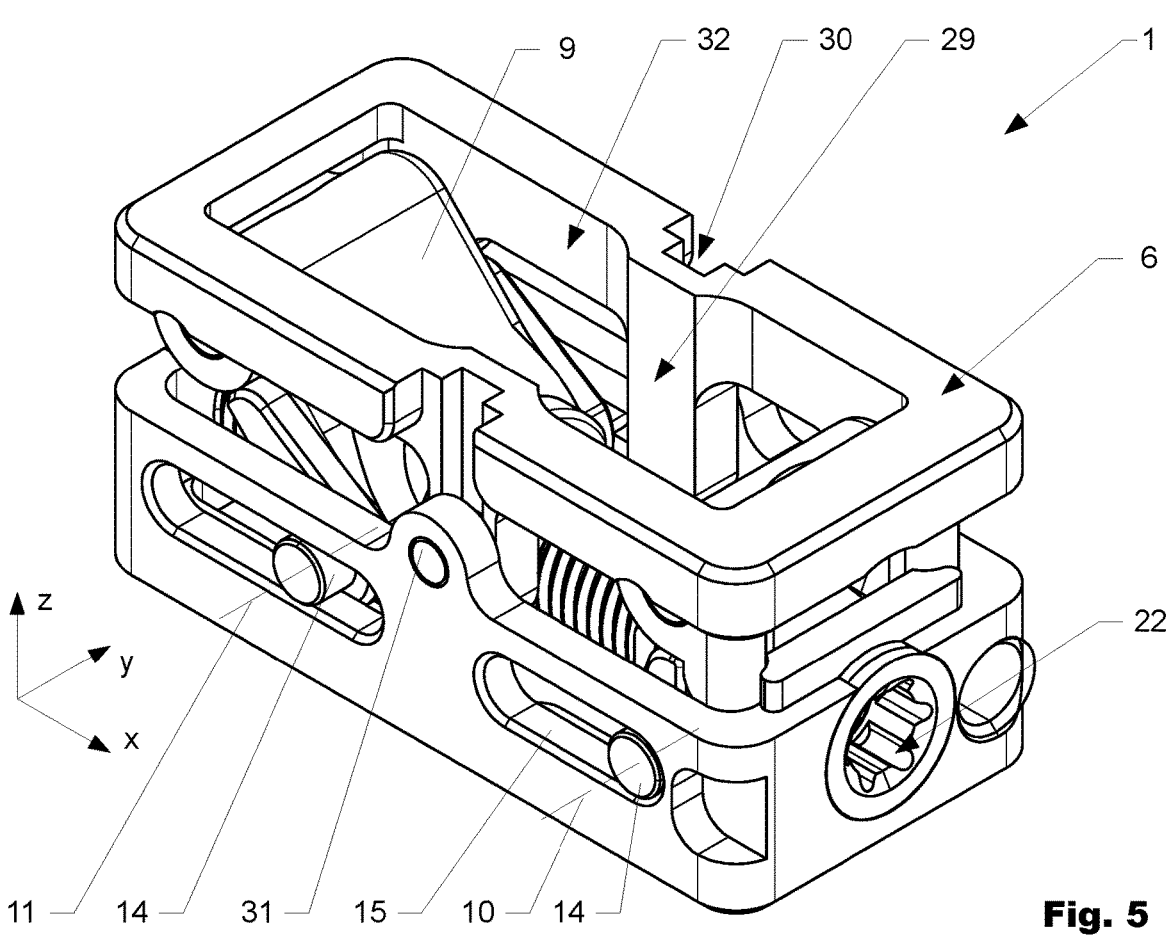
FIG. 5 shows the expandable intervertebral cage according to FIG. 4 in a perspective view.

FIG. 3 shows the expansion mechanism 4 in detail. The expansion mechanism 4 comprises a shaft 20 extending in a second direction (x-direction) with a bushing 21 arranged on the shaft 20. Thereby, a first thread 16 is arranged on an outer surface of the bushing 21 and second thread 17 is arranged on an outer surface of the shaft 20. This allows that the first and the second thread 16, 17 to operate independently from each other, if needed. The bushing 21 and the shaft 20 both rotate around a center axis, however both threads 16, 17 have different thread directions. The usage of threads 16, 17 in the expansion mechanism 4 allows in particular a continuous expansion from the retracted state of the cage 1 towards at least one expanded state of the cage 1. A distal end 25 of the bushing 21 is pivotably mounted in a first bearing opening 26 of the circumferential side wall 7 and a distal end 24 of the shaft 20 is pivotably mounted in a thereto opposite second bearing opening 27 of the circumferential side wall 7. To displace the stage 3 with respect to the base 2 the shaft 20 and/or the bushing 21 can be rotated with the help of a tool inserted through the opening 27 in the circumferential side wall 7 and into a first and/or second tool interface 22, 23. If the shaft 20 and the bushing 21 are rotated, a first nut 18 placed on the first thread 16 of the bushing 21 and the second nut 19 placed on the second thread 17 of the shaft 20 are displaced on the respective threads 16, 17. The usage of the nuts 18, 19 is advantageous, since the nuts 18, 19 can (self-) lock the cage 1 in an expanded stage preventing unwanted collapsing of the cage 1. By displacing the nuts 18, 19 on the threads 16, 17 a first lever 8 and a second lever 9 each interconnected by a base swivel joint 10, 11 to the base 2 and by a stage swivel joint 12, 13 to the stage 3, are moved such that the stage 3 lifts of the base 2. Meanwhile the first and the second lever 8, 9 are arranged in a space saving manner behind each other extending essentially in the same direction in the retracted state and unfold and extend out of the base 2 in an expanded state, as can be seen in FIG. 4. During the expansion, the base swivel joint 10 of the first lever 8 and the base swivel joint 11 of the second lever 9, which are arranged displaceable with respect to each other in a second direction (x-direction) perpendicular to the first direction (z-direction), are displaced away from each other, as can be seen in FIGS. 1-5. Each base swivel joint 10, 11 comprises two pivot bolts 14 arranged coaxially of each other and each guided within a guiding slot 15 in the side wall 7.

In FIG. 4, the maximum (essentially parallel) displacement of the second bone interaction surface 6 with respect to the first bone interaction surface 5 is displayed. As can be seen, only the base swivel joint 10 of the first lever 8 has reached its maximum displacement on the right hand side of the respective guiding slot 15. Hence, a (maximal) displacement distance of the base swivel joint 10 of the first lever 8 is smaller than a (maximal) displacement distance of the base swivel joints 11 of the second lever 9. Thus, the stage 3 (respectively the second bone interaction surface 6) can still be tilted by displacing the base swivel joints 11 even further, as illustrated in FIGS. 6-7.

In order to continuously tilt the stage 3 further, the shaft 20 (respectively the second thread 17) can be rotated separately from the bushing 21 (respectively the first thread 16). As a results, the second nut 19 arranged on the second thread 17 is displaced further than the first nut 18 on the first thread 16. Respectively the guiding slot(s) 15 of the base swivel joint 11 of the second lever 9 is longer than the respective guiding slot 15 of the base swivel joint 10 of the first lever 8, as can be seen in FIG. 4. If the second lever 9 is extended fully, also the pivot bolts 14 of the base swivel joint 11 of the second lever 9 is displaced to a maximum towards the left hand side of the cage 1, as e.g., illustrated in FIG. 6. Thus, the respective base swivel joints 10, 11 now have the largest possible distance from each other.

For a better stability of the expandable intervertebral cage 1, a linear guiding structure 28 may be present. The linear guiding structure 28 stabilizes the intervertebral cage in an expanded state and prevents unwanted lateral tilting or collapsing of the cage 1. In the shown embodiment, the linear guiding structure 28 comprises two struts 29 extending from the stage 3 into the circumferential side wall 7. The struts 29 are arranged opposite of each other with respect to the circumferential side wall 7. For a space saving design, the two struts 29 are further placed in the second direction between the first and the second lever 8, 9. Each strut 29 comprises a notch 30 extending in a longitudinal direction of the strut 29, wherein the notch 30 is interconnected to the circumferential side wall 7 by a pin 31 configured to slide in the notch 30 of the strut 29. The pin 31 is arranged on an inner surface of the circumferential side wall 7. If the cage 1 is in a tilted state (respectively the second bone interaction surface 6 has a tilting angle to the first bone interaction surface 5) the pin 31 remains in the notch 30 rotated with respect to the notch 30, as e.g., be seen in FIG. 6.

Figures 6, 7:
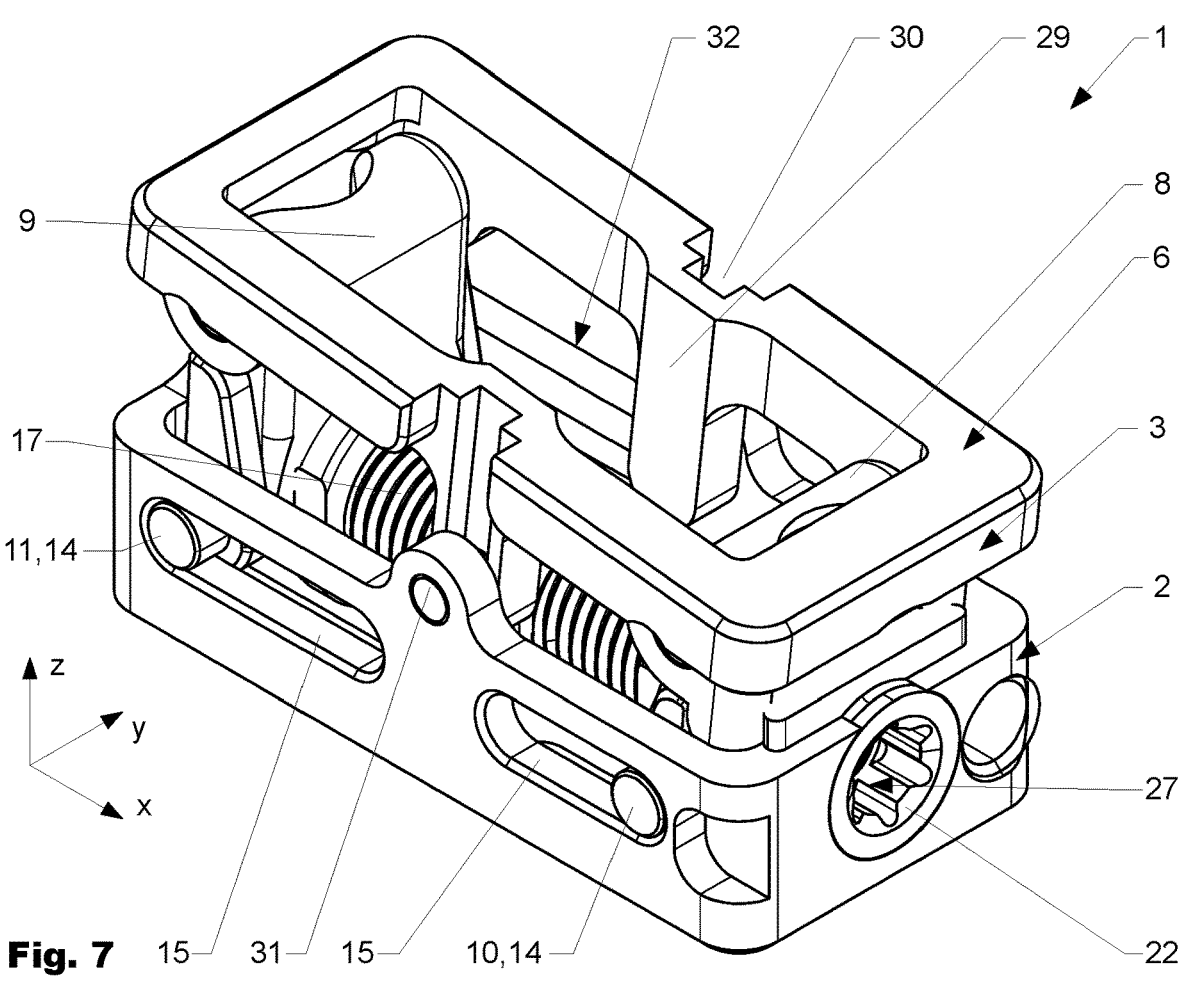
FIG. 6 shows the expandable intervertebral cage in a tilted expanded state in a side view.
FIG. 7 shows the expandable intervertebral cage according to FIG. 6 in a perspective view.

As e.g., seen in FIG. 7, the second bone interaction surface 6 is ring-shaped and circumvents an opening to access a filling room 32 for accommodating bone graft. Also, the first bone interaction surface may be ring-shaped and can circumvents an opening to access a filling room for accommodating bone graft (not shown).

Figure 8:
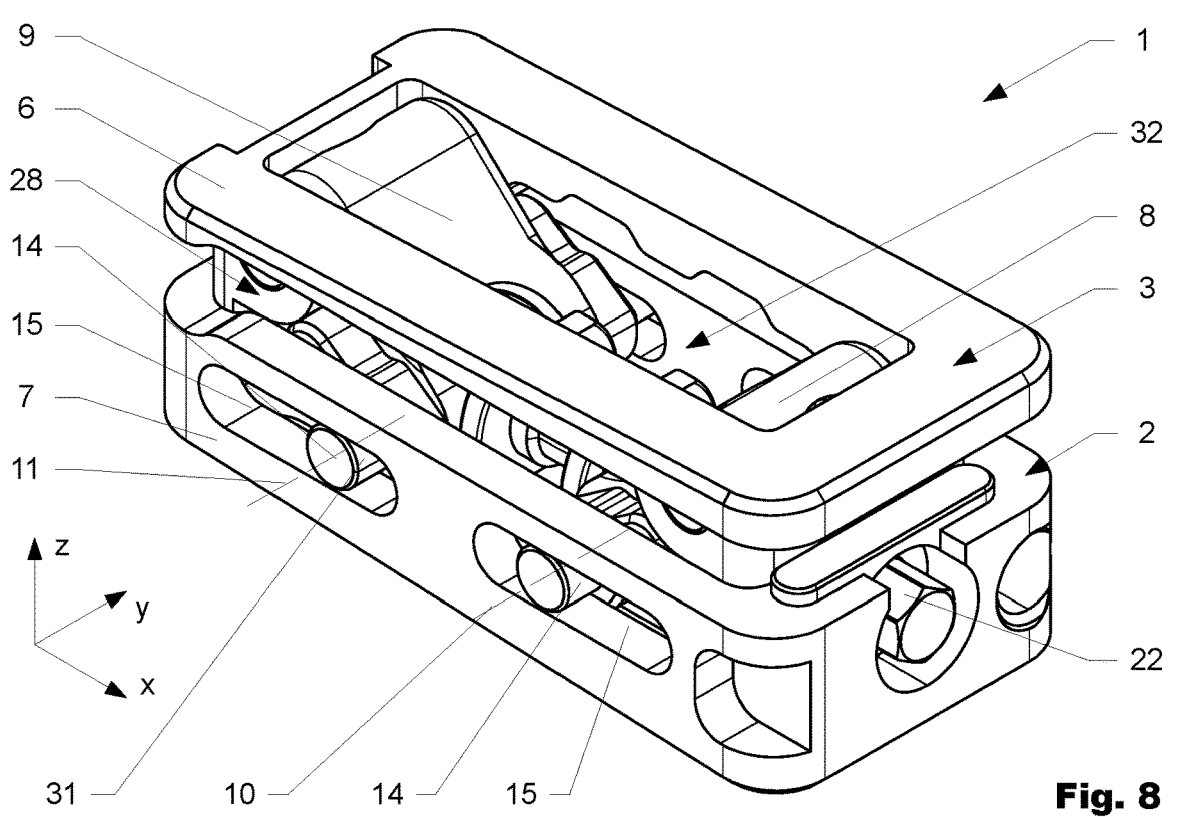
FIG. 8 shows a further variation of an expandable intervertebral cage according to the invention in a perspective view.
Figure 9:
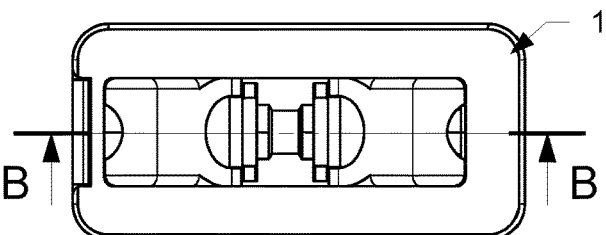
FIG. 9 shows the expandable intervertebral cage according to FIG. 8 in a top view.
Figure 10:
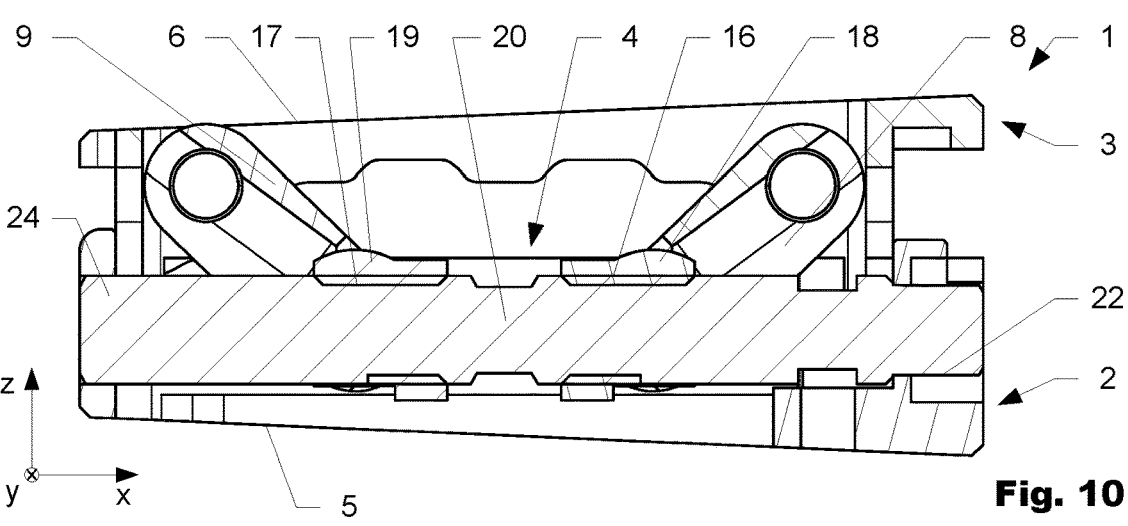
FIG. 10 shows the expandable intervertebral cage in a sectionized view B-B according to FIG. 9

FIGS. 8 to 10 show a further variation of an expandable intervertebral cage 1. The expandable intervertebral cage 1 differs from the first variation described in FIGS. 1 to 7 in that the expandable intervertebral cage 1 is only adjustable in the first direction, respectively adjustable in height. Thus, it is sufficient that the expansion mechanism 4 comprises a shaft 20 with a first and a second thread 16, 17 arranged on said shaft 20. In this case, the first and the second thread 16, 17 are interconnected to each other in a torque proof manner such that the first and second thread 16, 17 are operable simultaneously. The shaft 20 is pivotably mounted on both ends in bearing openings of the circumferential side wall. To displace the stage 3 with respect to the base 2 the shaft 20 can be rotated with the help of a tool inserted through the opening in the circumferential side wall 7 and into a tool interface 22. Equivalent to the first variation, a first nut 18 placed on the first thread 16 and a second nut 19 placed on the second thread 17 are displaced on the respective threads 16, 17 if the shaft 20 is rotated. By displacing the nuts 18, 19 a first lever 8 and a second lever 9 each interconnected by a base swivel joint 10, 11 to the base 2 and by a stage swivel joint 12, 13 to the stage 3, are moved such that the stage 3 lifts of the base 2. Thus, by rotating the shaft 20 the first and second lever 8, 9 are extended simultaneously and the second bone interaction surface 6, respectively the stage 3, is lifted with respect to the first bone interaction surface 5, respectively the base 2. As can be seen in FIG. 10, the first and second bone interaction surface 5, 6 can be angled with respect to each other. The angle between the first and second bone interaction surface 5, 6 can be the same in the retracted and expanded state of the cage.

Figure 11:
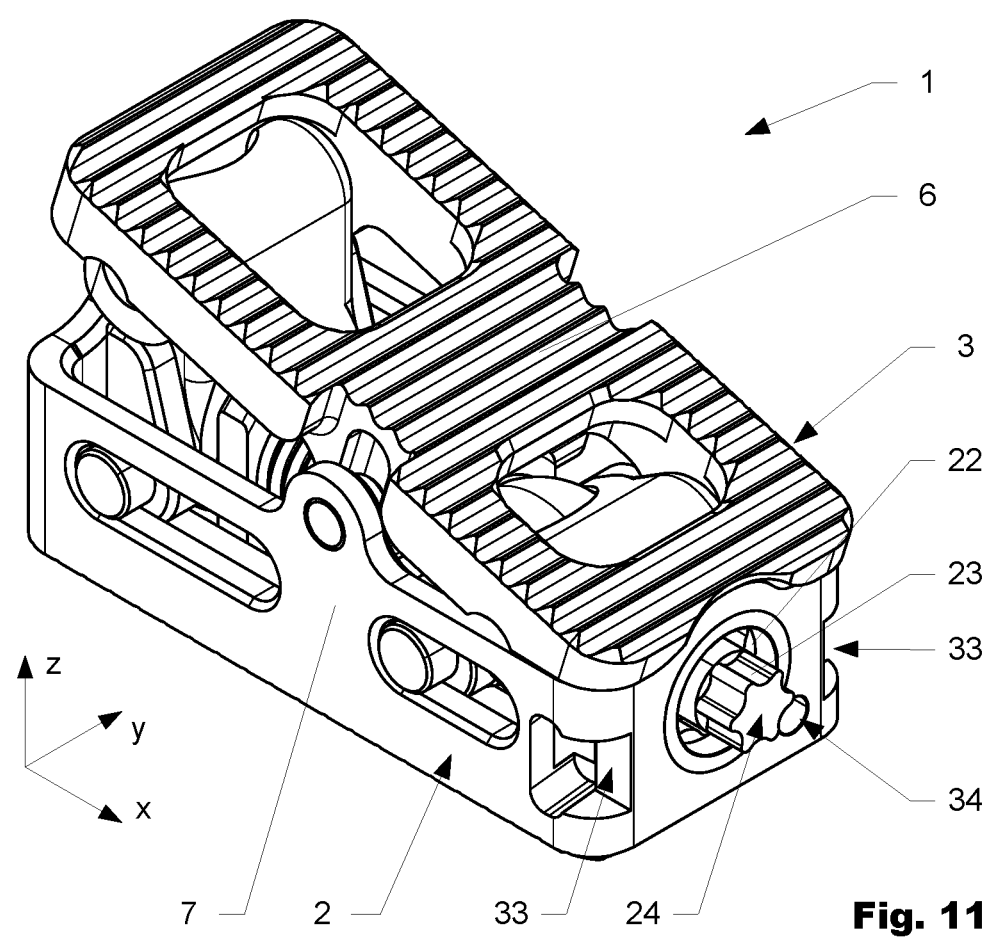
FIG. 11 shows a further variation of an expandable intervertebral cage according to the invention in a perspective view.
Figure 12:
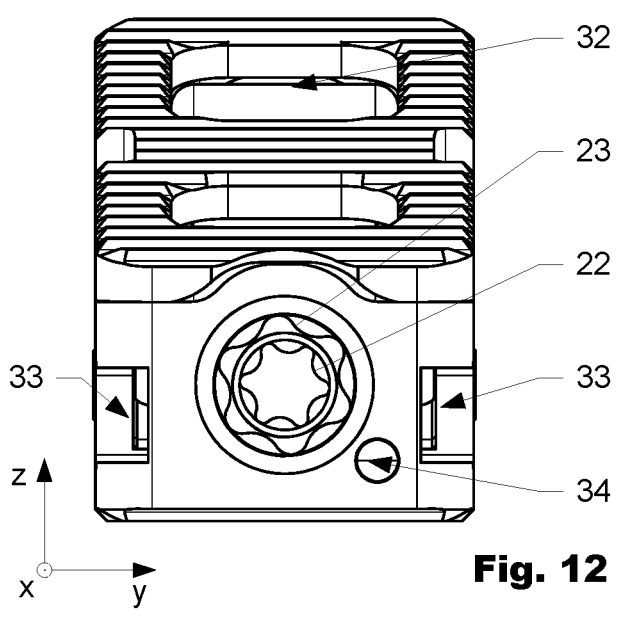
FIG. 12 shows the expandable intervertebral cage according to FIG. 11 in a side view.

FIGS. 11 and 12 illustrate a third variation of the intervertebral cage 1. The third variation differs from the variations explained above in that the cage 1 features different tool interfaces 22, 23. However, regarding the other elements of the cage 1, reference is made to the explanations given above with respect to the first and second variation of cage 1.

As can be seen, the intervertebral cage 1 according to the third variation comprises a first tool interface 22 with an inner surface and a second tool interface 23 with an outer surface. The inner and/or the outer surface are each hexalobular shaped if viewed from the second direction. Furthermore, the first and second tool interface 22, 23 are arranged consecutive in the second direction, with second tool interface 23 being arranged further outside than the first tool interface 22. Hereby, the second tool interface 23 even protrudes from the circumferential side wall 7. Furthermore, the intervertebral cage 1 comprises two positioning interfaces 33 on the circumferential side wall 7 to engage at least partly with a tool for inserting and positioning of the cage 1. The positioning interfaces 33 are thereby arranged opposite from each other with respect to the tool interfaces 22, 23. Furthermore, the cage 1 may comprise a locking element 34 (here designed as a threaded hole extending in the circumferential side wall 7), as explained above.

The invention claimed is:

1. An expandable intervertebral cage (1) comprising:

a base (2) comprising a peripheral circumferential side wall (7) extending in a first direction (z) and a first bone interaction surface (5);

a stage (3) comprising a second bone interaction surface (6) arranged opposite to the first bone interaction surface (5) with respect to the expandable intervertebral cage (1); and an expansion means (4) configured to adjust a position of the second bone interaction surface (6) of the stage (3) with respect to the first bone interaction surface (5) of the base (2) at least in the first direction (z) and arranged at least partially within the circumferential side wall (7) of the base (2), wherein the circumferential side wall (7) encompasses an inner space in which the expansion means is arranged in a retracted state of the expandable intervertebral cage (1), wherein the expansion means (4) comprises a first lever (8) and a second lever (9) each interconnected by a base swivel joint (10, 11) to the base (2) and by a stage swivel joint (12, 13) to the stage (3), wherein the base swivel joint (10) of the first lever (8) and the base swivel joint (11) of the second lever (9) are arranged displaceable with respect to each other in a second direction (x) perpendicular to the first direction (z), wherein the base swivel joints (10,11) each comprise two opposite pivot bolts (14) arranged coaxially with respect to each other extending in a third direction (y) perpendicular to the second direction (x) and being arranged linearly displaceable in a respective guiding slot (15) of the circumferential side wall (7) of the base (2), wherein the expansion means comprises a first thread (16) having a positive thread direction arranged in the second direction (x) and a thereto coaxially arranged second thread (17) having a negative thread direction, wherein the first thread (16) is interconnected to the base swivel joint (10) of the first lever (8) and the second thread (17) is interconnected to the base swivel joint (11) of the second lever (9) to displace the base swivel joints (10, 11) with respect to each other, and wherein a first nut (18) is arranged on the first thread (16) to interconnect the base swivel joint (10) of the first lever (8) to the first thread (16) and a second nut (19) is arranged on the second thread (17) to interconnect the base swivel joint (11) of the second lever (9) to the second thread (17).

2. The expandable intervertebral cage (1) according to claim 1, wherein the first thread and the second thread (16, 17) are interconnected to each other in a torque proof manner.

3. The expandable intervertebral cage (1) according to claim 1, wherein the base swivel joint (10) of the first lever (8) is linearly displaceable a first displacement distance (a) and the base swivel joint (11) of the second lever (9) is linearly displaceable a second displacement distance (b), wherein the first and the second displacement distances have different lengths.

4. The expandable intervertebral cage (1) according to claim 1, wherein the first thread and the second thread (16, 17) are arranged rotatable relative to each other.

5. The expandable intervertebral cage (1) according to claim 4, wherein the first thread (16) extends into a shaft (20) on which a bushing (21) is arranged comprising the second thread (17) on an outer surface, wherein the shaft (20) comprises the first thread (16).

6. The expandable intervertebral cage (1) according to claim 5, wherein the bushing (21) comprises a first tool interface (22) and the shaft (20) comprises at a free end a second tool interface (23) arranged adjacent to the first tool interface (22) and are configured to be operated by the same tool.

7. The expandable intervertebral cage (1) according to claim 6, wherein the first tool interface (22) has a hexalobular shaped inner surface, and the second tool interface (23) has a hexalobular shaped outer surface.

8. The expandable intervertebral cage (1) according to claim 5, wherein a distal end (25) of the bushing (21) is pivotably mounted in a first bearing opening (26) of the circumferential side wall (7) and the distal end (24) of the shaft (20) is pivotably mounted in a second bearing opening (27) of the circumferential side wall (7).

9. The expandable intervertebral cage (1) according to claim 1, wherein the expandable intervertebral cage (1) comprises a linear guiding structure (28) to prevent unwanted lateral tilting.

10. The expandable intervertebral cage (1) according to claim 9, wherein the linear guiding structure (22) comprises a strut (29) extending from the stage (3) into the circumferential side wall (7).

11. The expandable intervertebral cage (1) according to claim 10, wherein the strut (29) comprises a notch (30) extending in a longitudinal direction of the strut, wherein the notch (30) is interconnected to the circumferential side wall (7) by a pin (31) configured to slide in the notch (30) of the strut (29).

12. The expandable intervertebral cage (1) according to claim 1, wherein the first bone interaction surface (5) and/or the second bone interaction surface (6) circumvent at least partly an opening of a filling chamber (32) for accommodating bone graft.

* * * * *